United States Patent [19]

Schwertfeger et al.

[11] Patent Number: 4,987,254

[45] Date of Patent: Jan. 22, 1991

[54] FLUORINATED CARBOXYLIC ACID FLUORIDES

[75] Inventors: Werner Schwertfeger, Langgöns; Klaus Hintzer, Burgkirchen; Peter Blickle, Kelkheim, all of Fed. Rep. of Germany

[73] Assignee: Hoechst Aktiengesellschaft, Frankfurt am Main, Fed. Rep. of Germany

[21] Appl. No.: 389,367

[22] Filed: Aug. 3, 1989

[30] Foreign Application Priority Data

Aug. 6, 1988 [DE] Fed. Rep. of Germany ....... 3826807

[51] Int. Cl.$^5$ .............................................. C07C 51/62
[52] U.S. Cl. ..................................... 562/851; 562/849; 562/850
[58] Field of Search ................... 562/850, 849, 851

[56] References Cited

U.S. PATENT DOCUMENTS

| 2,456,768 | 12/1948 | Chaney | 558/461 |
| 3,442,942 | 5/1969 | Sianesi et al. | 562/851 |
| 3,451,908 | 6/1969 | Sianesi et al. | 562/851 |

OTHER PUBLICATIONS

R. N. Haszeldine et al., *J. Chem. Soc.* (c): 1968 398–405.

H. Millaver et al., *Angew. Chem. Int. Ed. Engl.* 24: 161–179 (1985).

Hans Millauer et al., *Angewanete Chem.* Int.'l Ed Engl., vol. 24, pp. 161–179 (1985).

Filyakova et al., *Chem. Abs.* 91:38844v (1979).

Daikin Kogyo Co., Ltd., *Chemical Abs.* 94:102806a (1981).

*Primary Examiner*—Paul J. Killos

[57] ABSTRACT

Fluorinated carboxylic acid fluorides of the formula I

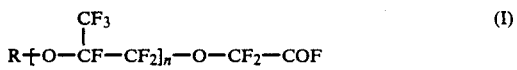

can be prepared from fluorinated vinyl ethers of the formula II

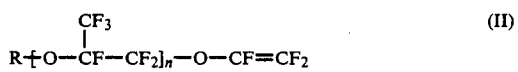

by reacting the vinyl ethers with an oxygen-containing gas in the presence of a catalytic amount of a Lewis acid. Perfluorinated carboxylic acids and derivatives thereof can be prepared from the carboxylic acid fluorides by secondary reactions, for example hydrolysis, esterification or aminolysis.

10 Claims, No Drawings

FLUORINATED CARBOXYLIC ACID FLUORIDES

DESCRIPTION

The invention relates to the preparation of fluorinated carboxylic acid fluorides from fluorinated vinyl ethers.

Fluorinated carboxylic acids and derivatives thereof have many possible uses in industry. The salts of long-chain perfluorinated carboxylic acids are employed as emulsifiers in the preparation of polytetrafluoroethylene, whilst fluorinated carboxylic acids in the form of their acid fluorides are needed for the synthesis of fluorinated vinyl ethers. Fluorinated carboxylic acids are converted into the corresponding Kolbe products, which are used as inert liquids or as solvents for fluorinated resins, and perfluorinated carboxylic acid fluorides are converted into perfluorinated inert liquids by exposure to light.

Fluorinated carboxylic acid fluorides containing ether groups are formed by reaction of fluorinated acid fluorides with fluorinated epoxides, for example hexafluoropropene oxide (HFPO) or tetrafluoroethylene oxide (TFEO). If HFPO is used, the products are always branched, whereas TFEO is a substance which is difficult to prepare and handle (compare H. Millauer et al., Angew. Chem., Int. Ed. Engl. 24, (1985) 161; and P. Tarrant et al., Fluor. Chem. Rev., 5 (1971) 77).

As is known, perfluorinated olefins do not give oxygen-containing compounds in the presence of oxygen and a Lewis acid, such as $SbF_5$. However, isomerization occurs (compare CA 91 38844v; CA 94 102806a).

There was thus the object of discovering a process for the preparation of fluorinated carboxylic acids and derivatives thereof, which starts from starting materials which are used industrially and is capable of providing fluorinated carboxylic acid fluorides of various structures using only one type of reaction.

It has been found that fluorinated vinyl ethers form fluorinated carboxylic acid fluorides in the presence of an oxygen-containing gas and with the aid of a catalytic amount of a Lewis acid.

The invention thus relates to the process according to the claims.

Fluorinated carboxylic acid fluorides of the formula I

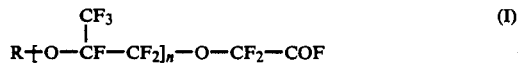

in which R denotes a branched or non-branched perfluorinated radical having 1–10, preferably 1–7, carbon atoms, in which one or more fluorine atoms can be replaced by other halogen atoms or a hydrogen atom, and n is an integer from zero to 10, preferably from 1 to 5 and in particular is 1 or 2, are prepared from vinyl ethers of the formula II

with R and n according to formula I, in the presence of a catalytic amount of a Lewis acid, for example $SbF_5$, $TiCl_4$, HF or $BF_3$ or mixtures of Lewis acids, by reaction with an oxygen-containing gas, preferably $O_2$ or air.

The reaction of the vinyl ether of the formula II is carried out in a vessel of glass, metal or plastic.

Examples of glass vessels which are used are columns, reaction tubes and flasks. The flasks are provided with a magnetic stirrer, thermometer, condenser and gas inlet tube.

The vinyl ether is introduced into the reaction vessel and the oxygen-containing gas is passed in. The progress of the reaction is monitored by withdrawing samples and analyzing these samples by gas chromatography or infrared spectral analysis. The catalyst is added at the start of the introduction, but can also be metered in subsequently if the conversion of the vinyl ether is not yet complete or the rate of reaction is no longer sufficiently high. It is advantageous to stir the mixture throughout the entire reaction. The reaction is carried out in a temperature range from $-50°$ to $+200°$ C., preferably from $0°$ to $100°$ C., under normal, reduced or increased pressure, preferably under normal or increased pressure.

The catalyst is employed in amounts of 0.01 to 20 mol %, based on the vinyl ether.

If autoclaves are used, the reaction is carried out under an increased pressure of an oxygen-containing gas, preferably oxygen and air, in particular oxygen.

The reaction according to the invention gives compounds of the formula I which were previously to be prepared only by reaction of tetrafluoroethylene oxide (TFEO)

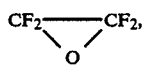

which is difficult to prepare and handle, with fluorinated carboxylic acids or ketones.

After the reaction, the products can be converted into their corresponding carboxylic acids or derivatives thereof, for example esters and amides, preferably esters, by secondary reactions, for example hydrolysis, esterification or aminolysis, preferably esterification.

EXAMPLES

Example 1

133 g (0.5 mol) of $CF_3-CF_2-CF_2-O-CF=CF_2$ (perfluoropropyl vinyl ether=PPVE) were initially introduced into a glass flask fitted with a magnetic stirrer, thermometer, low temperature condenser and gas inlet tube. Oxygen was then passed in at room temperature and about 100 mg of $SbF_5$ were added. An exothermic reaction started immediately and the mixture started to boil. When the reaction had subsided, the mixture was left to stand overnight at room temperature. A sample of the mixture was esterified with methanol, during which the $CF_3-CF_2-CF_2-O-CF_2-COF$ formed during the reaction was esterified to $CF_3-CF_2-CF_2O-CF_2-COOCH_3$, and a gas chromatogram (WLD) was then recorded. The composition found was:

83% of PPVE
3% of $CF_3-CF_2-COOCH_3$
13% of $CF_3-CF_2-CF_2-O-CF_2-COOCH_3$.

The entire batch was then esterified with methanol and distilled, during which the $CF_3-CF_2-CF$-

2—O—CF$_2$—COOCH$_3$ had a boiling point of 102°–104° C. The yield of the ester was 9 g.

Example 2

108 g (0.2 mol) of perfluoropropoxypropyl vinyl ether

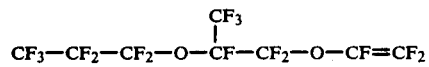

(PPVE-2) were initially introduced into the apparatus according to Example 1 at room temperature and oxygen was passed in. About 100 mg of SbF$_5$ were then added. After the reaction, a further 100 mg of SbF$_5$ were added, whereupon the temperature inside the flask rose to 60° C. When the reaction had ended, all the volatile constituents were distilled off under 10–15 mbar into a cold trap which had a temperature of −78° C.

The cold trap contained 103 g of a colorless liquid. A sample of the batch was esterified with methanol and a gas chromatogram (WLD) was then recorded. The composition found was:

44% of PPVE-2

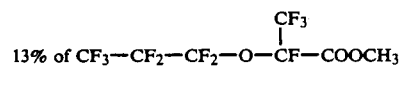

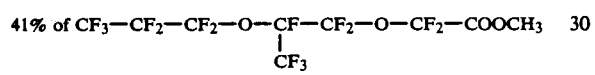

The entire batch was then esterified with methanol and distilled, during which

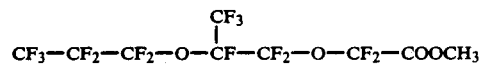

had a boiling point of 91°–92° C. under 133 mbar.

Example 3

100 g of

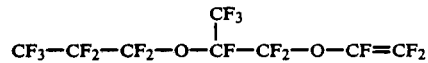

(PPVE-2) were initially introduced into a 100 ml glass flask with a magnetic stirrer, thermometer, low temperature condenser and short gas inlet tube. After addition of 1.5 g of SbF$_5$, air was passed in. An exothermic reaction occurred. The air passed in was replaced by pure oxygen. The exothermic reaction became significantly more vigorous. The maximum internal temperature reached was 68.4° C. COF$_2$ was detected in the issuing gas with the aid of IR spectroscopy. When the exothermic reaction has subsided, 1 g of SbF$_5$ was added, after which an exothermic reaction started again. This operation was repeated once more. Thereafter, no further PPVE-2 was detectable in the contents of the flask by IR spectroscopy. All the volatile constituents were extracted from the reaction flask under 10 mbar into a cold trap kept at −78° C. The contents of the trap (87 g) were esterified with methanol, washed with water and dried over sodium sulfate. The gas chromatogram (WLD) of the esterified mixture showed, in addition to 4% of PPVE-2,

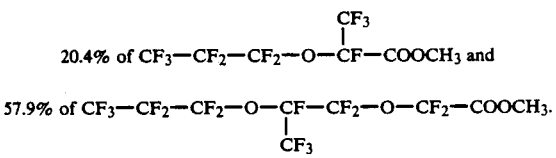

Distillation gave

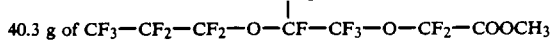

with a boiling point of 78° C./67 mbar.

Example 4

108 g (0.25 mol) of PPVE-2 were initially introduced into the apparatus according to Example 1 at room temperature and oxygen was passed in. About 1 g of TiCl$_4$ was then added.

During the exothermic reaction, oxygen was taken up. A sample of the batch was esterified with methanol and a gas chromatogram (WLD) was then recorded. The composition found was:

76% of PPVE-2

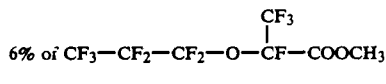

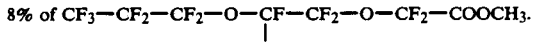

After the reaction, the batch was distilled in vacuo into a cold trap and a $^{19}$F-NMR spectrum of the contents (78 g) was recorded, confirming the result of the gas chromatography analysis. The spectrum also showed the signal for COF$_2$.

Example 5

108 g (0.25 mol) of PPVE-2 and 1 g of anhydrous HF were introduced into a polyethylene vessel. After thorough shaking, 9 g of the lower phase were introduced into a 200 cm$^3$ autoclave of stainless steel and heated at 50° C. under an oxygen pressure of 10 bar for 20 hours.

After cooling, a sample of the liquid contents of the autoclave was esterified and a gas chromatogram (WLD) was then recorded. The composition found was:

70% of PPVE-2

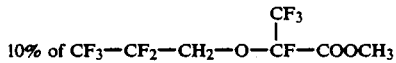

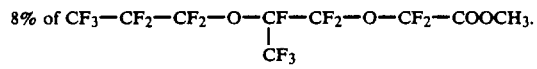

Example 6

104.4 g (0.3 mol) of H—(CF$_2$)$_5$—O—CF=CF$_2$ were initially introduced into the apparatus according to Example 1 at room temperature and oxygen was passed in. Two 100 mg portions of SbF$_5$ were then added, whereupon an exothermic reaction started.

The batch was esterified with methanol. During this operation, the H(CF$_2$)$_4$—O—CF$_2$—COF formed in the reaction was esterified to H—(CF$_2$)$_4$—O—CF$_2$—COOCH$_3$. Thereafter, the batch was washed with water and dried over Na$_2$SO$_4$. A gas chromatogram (WLD) was then recorded. The following composition was found:

60% of H—(CF$_2$)$_5$—O—CF=CF$_2$
10% of H—(CF$_2$)$_4$—COOCH$_3$
27% of H—(CF$_2$)$_5$—O—CF$_2$—COOCH$_3$.

On distillation, the ester H—(CF$_2$)$_5$—O—CF$_2$—COOCH$_3$ had a boiling point of 163°–166° C.

Example 7

About 100 mg of SbF$_5$ were added to 55.4 g (0.2 mol) of Br—CF$_2$—CF$_2$—O—CF=CF$_2$ under air in the apparatus according to Example 1. After the weakly exothermic reaction, a weak stream of air was passed into the apparatus.

After a reaction time of 20 hours at room temperature, the batch was esterified with methanol. After working up with water and drying, a gas chromatogram (WLD) was recorded. The composition found was:

48% of Br—CF$_2$—CF$_2$—O—CF=CF$_2$
10% of Br—CF$_2$—COOCH$_3$
39% of Br—CF$_2$—CF$_2$—O—CF$_2$—COOCH$_3$

On distillation, the ester Br—CF$_2$—CF$_2$—O—CF$_2$—COOCH$_3$ had a boiling point of 126°–131° C.

Example 8

1 g of SbF$_5$ was added to 50 g (0.18 mol) of Br—CF$_2$—CF$_2$—O—CF=CF$_2$ in the apparatus of Example 1 and oxygen was passed in. When the exothermic reaction had subsided, a further 1 g of SbF$_5$ was added. When the exothermic reaction which occurs again had ended, all the volatile constituents were extracted under 67 mbar into a cold trap cooled with dry ice. At room temperature, the trap contained 40 g of colorless liquid. A sample was esterified with methanol and analyzed with the aid of gas chromatography (WLD). The sample contained 3.1% of Br—CF$_2$—CF$_2$—O—CF=CF$_2$
26.5% of Br—CF$_2$—COOCH$_3$
63.8% of Br—CF$_2$—CF$_2$—O—CF$_2$—COOCH$_3$

Comparison Example 50 g of a mixture of isomeric perfluoroheptenes which, according to the gas chromatogram and the $^{19}$F-NMR spectrum, was composed of CF$_3$—(CF$_2$)$_4$—CF=CF$_2$ and CF$_3$—(CF$_2$)$_3$—CF=CF—CF$_3$ (cis and trans) in a molar ratio of 10:6.2, were initially introduced into the apparatus according to Example 1 at room temperature and oxygen was passed in. About 100 mg of SbF$_5$ were then added. An exothermic reaction started immediately. When the reaction had subsided, the mixture was analyzed with the aid of $^{19}$F-NMR spectroscopy. No products which indicated a reaction with oxygen were detectable. Instead, exclusively the isomeric olefins CF$_3$—(CF$_2$)$_3$—CF=CF—CF$_3$ (cis and trans) were present.

We claim:

1. A process for the preparation of a fluorinated carboxylic acid fluoride of the formula I

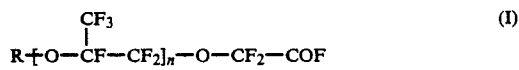

in which R denotes a branched or non-branched perfluorinated radical having 1–10 carbon atoms, in which one or more fluorine atoms can be replaced by other halogen atoms or a hydrogen atom, and n is an integer from zero to 10, which comprises reacting a vinyl ether of the formula II

with R and n according to formula I, with an oxygen-containing gas in the presence of a catalytic amount of a Lewis acid.

2. The process as claimed in claim 1, wherein the reaction is carried out in a temperature range from −50° C. to +200° C.

3. The process as claimed in claim 1, wherein the oxygen-containing gas is oxygen or air.

4. The process as claimed in claim 1, wherein the Lewis acid is employed in an amount of 0.01 mol % to 20 mol-%.

5. The process as claimed in claim 1, wherein the Lewis acid is SbF$_5$, TiCl$_4$, HF or BF$_3$, or mixtures thereof.

6. The process as claimed in claim 1, wherein R denotes a branched or non-branched per fluorinated radical having 1–7 carbon atoms.

7. The process as claimed in claim 1, wherein n is an integer from 1 to 5.

8. The process as claimed in claim 1, wherein n is an integer of 1 or 2.

9. The process as claimed in claim 2 wherein the reaction temperatures ranges from 0° C. to 100° C.

10. A process for the preparation of a fluorinated carboxylic acid fluoride of the formula I

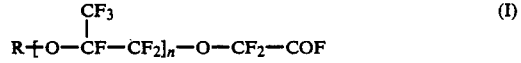

in which R denotes a branched or non-branched perfluorinated radical having 1–10 carbon atoms, in which one or more fluorine atoms can be replaced by other halogen atoms or a hydrogen atom, and n is an integer from zero to 10, which comprises reacting a vinyl ether of the formula II

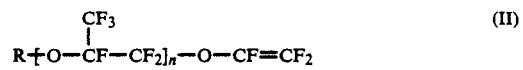

with R and n according to formula I, with an oxygen-containing gas in the presence of a catalytic amount ranging from 0.01 to 20 mol % of the vinyl ether of a Lewis acid.

* * * * *